United States Patent
Babnick et al.

(10) Patent No.: US 10,663,404 B1
(45) Date of Patent: May 26, 2020

(54) STANDOFF RAMAN SYSTEM (PRIED)

(71) Applicant: Alakai Defense Systems, Inc., Largo, FL (US)

(72) Inventors: Robert Dean Babnick, Largo, FL (US); Darius Vunck, Clearwater, FL (US); Robert Douglas Waterbury, Palm Harbor, FL (US); Timothy Molner, St. Petersburg, FL (US); Ed Dottery, Palm Harbor, FL (US)

(73) Assignee: Alakai Defense Systems, Inc., Largo, FL (US)

( * ) Notice: Subject to any disclaimer, the term of this patent is extended or adjusted under 35 U.S.C. 154(b) by 0 days.

(21) Appl. No.: 16/151,682

(22) Filed: Oct. 4, 2018

Related U.S. Application Data

(60) Provisional application No. 62/568,621, filed on Oct. 5, 2017.

(51) Int. Cl.
| | |
|---|---|
| *G01J 3/44* | (2006.01) |
| *G01N 21/65* | (2006.01) |
| *G01N 21/47* | (2006.01) |
| *G01N 33/22* | (2006.01) |
| *G01J 3/443* | (2006.01) |
| *G01J 3/02* | (2006.01) |
| *G01N 21/17* | (2006.01) |

(52) U.S. Cl.
CPC ............ *G01N 21/65* (2013.01); *G01J 3/0237* (2013.01); *G01J 3/0272* (2013.01); *G01J 3/44* (2013.01); *G01J 3/443* (2013.01); *G01N 21/474* (2013.01); *G01N 33/227* (2013.01); *G01J 2003/4424* (2013.01); *G01N 2021/1793* (2013.01); *G01N 2021/655* (2013.01); *G01N 2201/06113* (2013.01)

(58) Field of Classification Search
CPC .... G01N 21/65; G01N 21/474; G01N 33/227; G01N 2021/1793; G01N 2201/06113; G01N 2021/655; G01J 3/0272; G01J 3/44; G01J 3/0237; G01J 3/443; G01J 2003/4424; G01J 3/28; G01J 3/26
See application file for complete search history.

(56) References Cited

U.S. PATENT DOCUMENTS

| | | |
|---|---|---|
| 8,125,627 B2 | 2/2012 | Dottery et al. |
| 9,052,290 B2 * | 6/2015 | Treado ...................... G01J 3/02 |

(Continued)

OTHER PUBLICATIONS

Verkouteren, Jennifer R., "Particle Characteristics of Trace High Explosives: RDX and PETN*", J Forensic Sci, vol. 52, No. 2, pp. 335-340, Mar. 2007.

(Continued)

*Primary Examiner* — Abdullahi Nur
(74) *Attorney, Agent, or Firm* — McKee, Voorhees & Sease, PLC

(57) ABSTRACT

The present invention relates to a highly portable, highly flexible standard of distance chemical detector such as can be used, for example, for standoff detection of explosives. Aspects of the invention include techniques for portability compactness and ways to diminish influence of fluorescence on Raman spectroscopy. Additional features can include a compact imaging spectrometer, a wirelessly connected smart device for user interface, and an auto-focus/range finder.

20 Claims, 12 Drawing Sheets

(56) References Cited

U.S. PATENT DOCUMENTS

2008/0151241 A1* 6/2008 Lindfors .............. G01N 21/718
                                                        356/318
2013/0128264 A1* 5/2013 Wax ................... G01B 9/02044
                                                        356/300
2016/0103073 A1  4/2016 Ford et al.

OTHER PUBLICATIONS

Verkouteren, et al., "Automated Mapping of Explosives Particles in Composition C-4 Fingerprints", J Forensic Sci, vol. 55, No. 2, 7 pages, 2010.
Thermo Scientific FirstDefender RM, Product Specifications, Thermo Scientific, 2 pages, 2012.
ACE-ID, Non-Contact Explosives & Narcotics Identifier with ORS Technology, Smiths Detection, 2 pages, 2016.
Verkouteren, "Particle Characteristics of Trace High Explosives: RDX and PETN", Abstract, www.nist.gov/publications/particle-characteristics-trace-high-explosives-rdx-and-petn, last accessed on Oct. 4, 2018, 1 page.

\* cited by examiner

STANDOFF RAMAN SYSTEM (PRIED)

CROSS-REFERENCE TO RELATED APPLICATIONS

This application claims the benefit of Provisional Application U.S. Ser. No. 62/568,621 filed on Oct. 5, 2017, all of which is herein incorporated by reference in its entirety.

I. BACKGROUND OF THE INVENTION

A. Field of the Invention

The present invention relates to methods and systems for detection of chemical compounds from stand-off distances and, in particular, to methods and systems utilizing direct imaging Raman spectroscopy in a highly portable configuration.

B. Problems in the State of the Art

1. Background

Use of Raman spectroscopy for detection of chemicals and chemical compounds nondestructively, including from standoff distances, is well known. An example is U.S. Pat. No. 8,125,627 to Alakai Defense Systems, Inc., incorporated by reference herein. In the case of detecting explosives, use of a laser as an illumination source allows a pinpointed collimated beam to interrogate the target surface from meters to hundreds of meters away. Reflectance along the same optical path can be collected and evaluated for Raman scattering. By correlations to calibration references, presence of explosives of interest can be made. Standoff distances promote safe interrogation of such targets.

Raman spectroscopy can be imaging or non-imaging. Direct imaging Raman spectrometers collect light with optics having a field of view of a target and image that field of view. The image (usually pixelated) is evaluated spectrographically for Raman content, particularly at predetermined wavelengths.

One type of direct imaging Raman spectroscopy uses a digital image sensor, essentially a digital camera having an imaging plane consisting of a matrix of minute pixels (e.g. CCD digital imager). With Raman techniques, and others, reflectance from a target is collected with optics (e.g. essentially a telescope or microscope) which has a field of view (FOV). Typical direct imaging systems tend to spatially correlate the FOV of the telescope with the pixels of the image of the FOV at the sensor imaging plane. This allows an understanding of which part of the image at the imaging plane correlates with which part of the target. However, this adds complexity to the system.

One way of translating collected light from the FOV of a Raman imaging spectrometer to the imaging plane is through a fiber optic bundle. One set of adjacent ends of fibers can be arranged to cover the FOV of the telescope (e.g. a circular pattern). The opposite ends can be aligned at the digital imager imaging plane. As mentioned, state of the art systems tend to use techniques to correlate each fiber end at the imaging plane with relative spatial position in the FOV. These correlations essentially create a spatial map of the FOV on a fiber-by-fiber basis.

2. Problem Statement

A well-known problem with evaluating reflectance from the target surface for Raman scattering is accurately separating the Raman signal from non-relevant parts including fluorescence caused by laser illumination of the target. A number of solutions have been suggested for extracting the Raman content in light of the fluorescent noise, including but not limited to the owner of the present application. Published US Patent Application 2016/0103073 to Alakai Defense Systems, Inc. and incorporated by reference herein, describes one such method. Additionally, fluorescence removal, and other noise removal, has been attempted in the processing of the collected reflectance which is typically transduced into an electrical or electronic signal representative of the reflectance. Digital signal processing algorithms can be used towards that end. However, the nature of Raman content is such that separating it from fluorescence and other noise is challenging. And fluorescence removal techniques have not been entirely successful.

Another challenge is environmental conditions at target locations. Sometimes targets are outdoors in harsh conditions. Sometimes electrical power grid service is unavailable. Sometimes portability is beneficial if not essential.

It could be advantageous to not have to rely on spatial mapping of optical fibers in direct imaging Raman spectroscopy.

However, a number of competing factors make it difficult to solve these issues. For example, spectroscopy involves sometimes sensitive optical components which take up significant space making it difficult or cumbersome to make portable or field-rugged. It can be difficult to solve the fluorescence noise problem without costly and complex components and techniques. There is therefore room for improvement in this technical area.

Systems and techniques for standoff distance optical chemical sensing/detection that address these challenges are proposed in the field of imaging Raman spectroscopy.

II. SUMMARY OF THE INVENTION

A. Objects, Features, and Advantages of the Solution of the Invention

A principal object of the present invention is to provide apparatus, systems, and methods for solving problems or overcoming deficiencies in the state-of-the-art regarding optical detectors.

As will be seen by reference to the following disclosure, the solutions of the present invention provide one or more of the following benefits:
   a. Does not rely on spatially mapping.
   b. Eschews spatial mapping.
   c. Does not have to rely on fluorescence removal techniques.
   d. Small form factor for portability and efficacy.
   e. Robust and rugged.
   f. Good optical detection performance.
   g. Effective communication of information to the user and effective user input related to operation of the system.
   h. Certain automatic features.

Additional options and features meaningful to standoff detection of chemicals, including explosives, are disclosed herein and will become more apparent with reference to the accompanying description and drawings.

B. Aspects of the Solution of the Invention

A first aspect of the invention relates to a system for chemical detection at standoff distances in a variety of environments. The system includes a portable housing containing an imaging spectrometer and portable electrical power supply. A hand-held-sized optical component includes a laser and optical collector/telescope to both interrogate a target surface with light energy and then collect and focus reflectance in the telescope's field of view for use by the spectrometer. A user interface, such as phone, smart watch, tablet, etc. can effectively present relevant information to the user and present system control options for operation of the system.

In another aspect of the invention, the ability of the system to distinguish chemical species of interest as well as diminish noise such as caused by fluorescence in the collected reflectance is proposed. A central feature is use of a bundle of a plurality of individual fiber optics between the telescope FOV and the detector plane of the spectrometer. First adjacent ends of the fiber optic bundle are arranged in a 2D plane (e.g. circular or other 2D pattern). Each fiber therefore essentially receives a portion of the overall image of the telescopes' FOV of the target surface and transmits that portion to an opposite end. Collectively, the first ends of fibers therefore receive the whole focused, collected reflectance from the telescope's FOV; which is compositely an image of the telescope's field of view. However, arrangement of opposite second ends of the fiber optics of the bundle can be changed from the 2D pattern to a different pattern (e.g. linear array). This linear pattern is presented as an input to the imaging spectrometer. Each portion of the telescope field-or-view image is therefore re-arranged into a different (e.g. linear) array of portions of the telescope FOV. The imaging spectrometer receives that linear array and can manipulate the transmitted portion of light from the output end of each fiber optic to a detection or imaging plane of a digital imager or sensor. The detection plane can be imaged by a digital imager and the individual portions of light from each fiber optic sent to a spectrometer to be individually spectrally evaluated. As will be further discussed below, breaking up the telescope FOV into individual portions of a 2D pattern, and then rearranging those portions to a linear array, allows a variety of benefits. One is improving the ability to distinguish signals of interest from noise such as fluorescence, including on a fiber optic by fiber optic basis. Another is high-performance resolution at the detector plane for the content of each fiber-optic. This resolution promotes more accuracy and precision in the spectral evaluation for chemical constituents of interest in each. Another benefit is ability to use the fiber optic bundle with a specific combination of optical components inside the spectrometer to create compactness of the spectrometer which, in turn, promotes high portability. Another is that, despite rearranging the fibers between telescope and imager, requirement of spatial correlation of opposite ends of each fiber is not needed. Another is a subtle, innovative discovery that at least some substances of interest may help mask or attenuate fluorescence that would otherwise occur in its absence. In the case of looking for trace amounts of molecular species of interest (e.g. such as trace amounts of explosives in a fingerprint on a suitcase), the imaging spectrometer looks for individual fiber optics that "light up" at wavelengths of interest, meaning that the signal amplitude at one or more wavelengths associated with Raman signal for such molecular species is clearly distinguishable from the same wavelength in the content of other fibers. The technique estimates that such "lit up" fiber has identified the molecular species. The technique thus does not have to rely on signal processing to try to remove background noise or fluorescence. It does not care about spatial correlation to FOV.

Another aspect of the invention relates to a highly adaptable user interface. Using processing and storage capability of a digital smart device such as watch, phone, or tablet, and wireless communication to the spectrometer, a wide variety of information can be displayed to the user, haptic capabilities such as vibration can be used for notification of states of detection analyses, and adjustment of the spectrometer or other components of the system can be conveniently instructed from that interface.

An optional feature usable with other aspects of the invention is an auto focus and range estimator. Typically, the image of the laser illumination source (typically monochromatic) collected by the telescope FOV in the reflectance from the target object is excluded (e.g. filtered) from the spectral analysis as it is irrelevant to chemical detection of substance(s) on the target. This aspect of the invention counter-intuitively takes advantage of this normally excluded content. It splits the collected reflectance, including the returned reflectance at the transmission frequency of the laser, from the optical axis of the telescope to an optical detector, such as a photodetector, dedicated to detect just the transmission wavelength of the laser. It assumes that when the telescope is correctly focused, the intensity of the collected laser light will be at its highest. In one embodiment, the telescope is focused by moving a secondary lens relative to a fixed primary lens. An electro-mechanical actuator can incrementally adjust the secondary lens relative to the primary lens along the optical axis. For each detection interrogation with the system, on on-board controller can instruct the actuator to move the secondary mirror, sometimes in either direction, until the photodetector indicates maximum intensity. This is an indirect way to achieve autofocusing by feedback of measured laser transmission wavelength intensity. The inventive technique also can be used to indirectly estimate range to target. Using the assumption that distance between the secondary mirror and primary mirror is proportional to range to target when focused, the system can be calibrated to generate a range-to-target estimate for any distance between secondary and primary mirrors. Determination of a focused state for the telescope can be based on the autofocus technique described above. The estimated range-to-target value can be communicated to the user interface and recorded, displayed, or otherwise used by the user or the system.

III. BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 3:
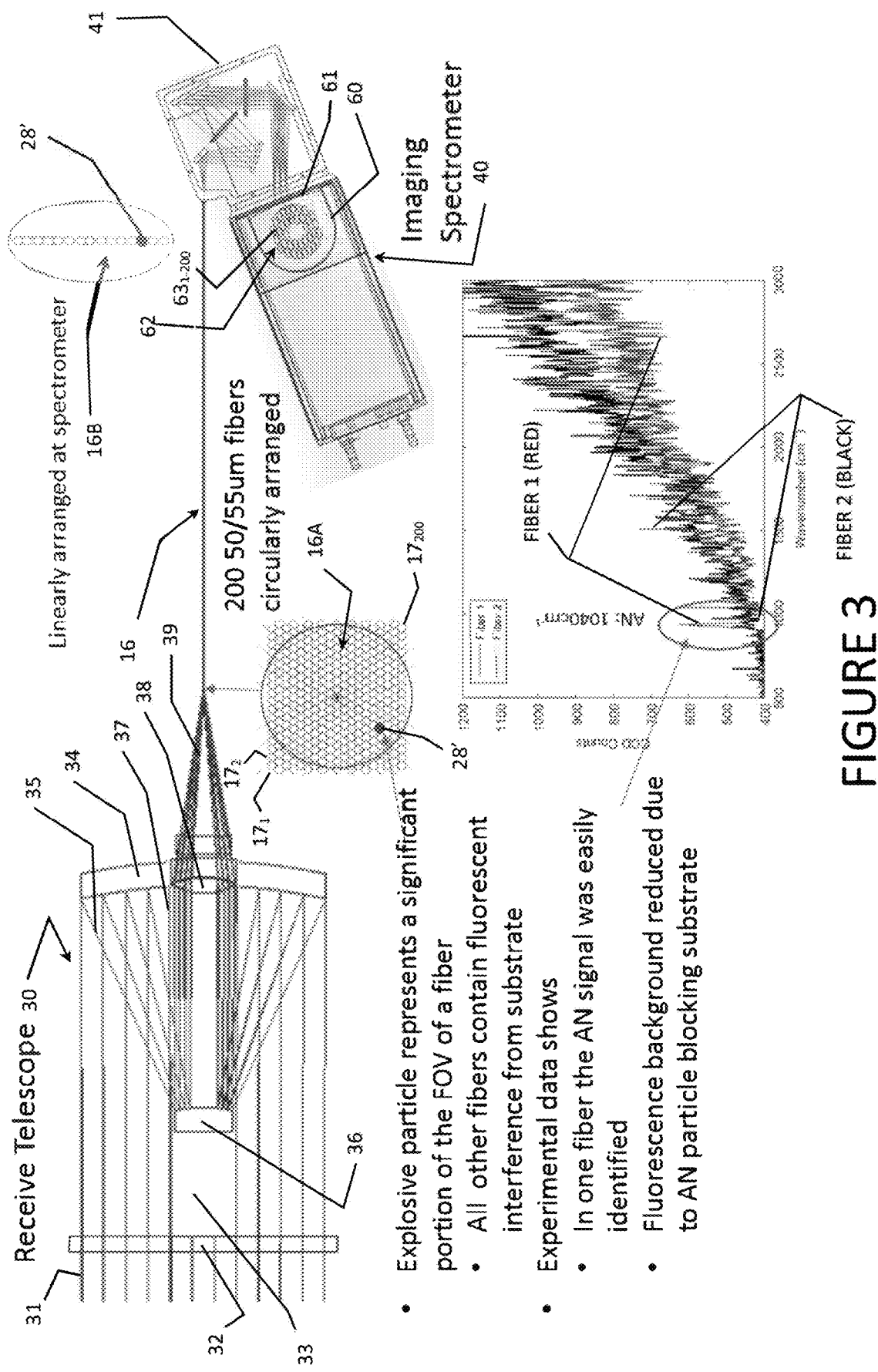

FIG. 3 is: (top) description of Raman detection system showing the multiple fiber array between the collection optics (telescope) and spectrometer. (bottom) Comparison of the spectra from two individual fibers. The AN feature (circled) are easily identified from the noise. The fluorescence is reduced in the fiber that does not contain AN.

Figure 4A:
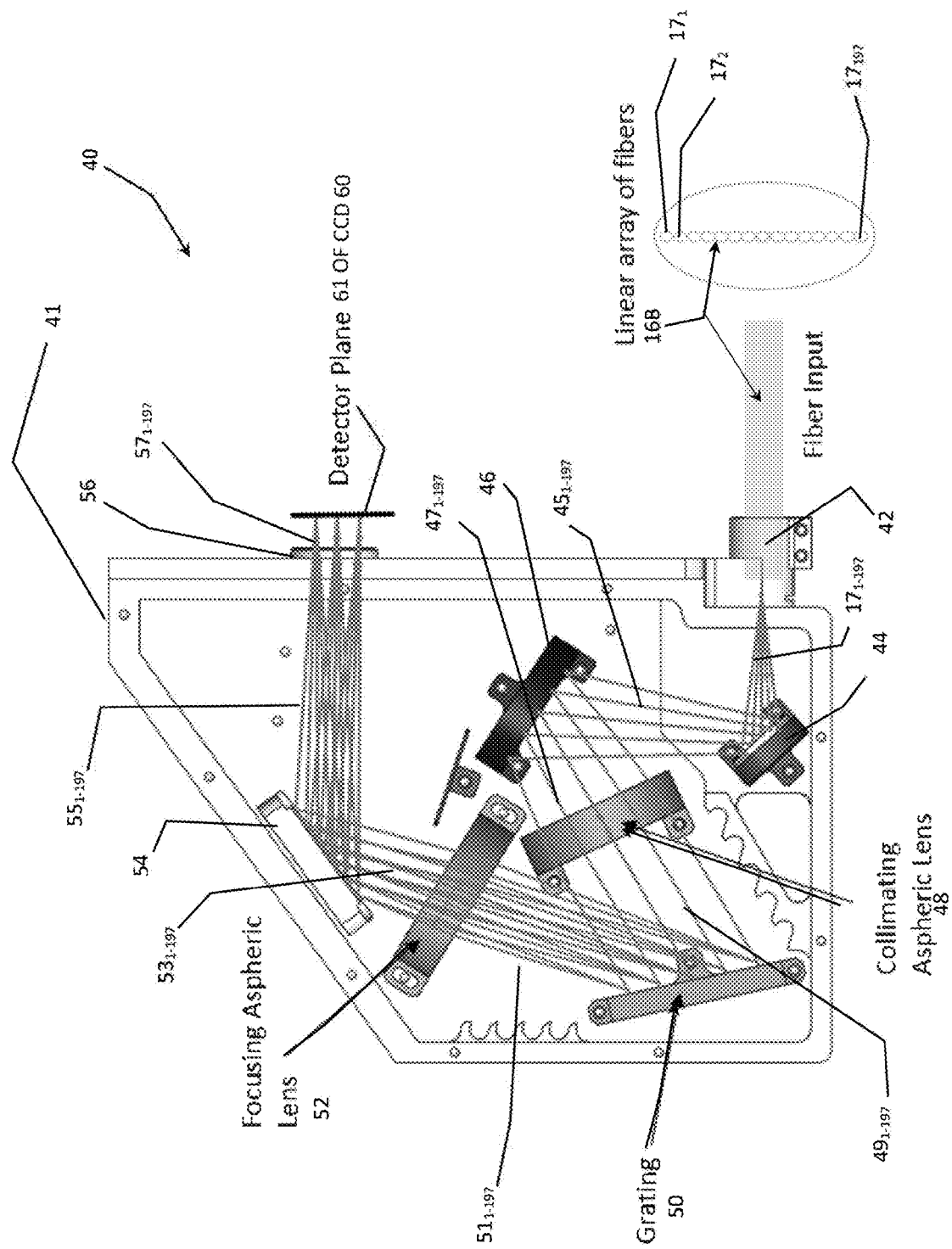

FIG. 4A is a layout of an Imaging Spectrometer according to one embodiment of the invention.

Figure 4B:
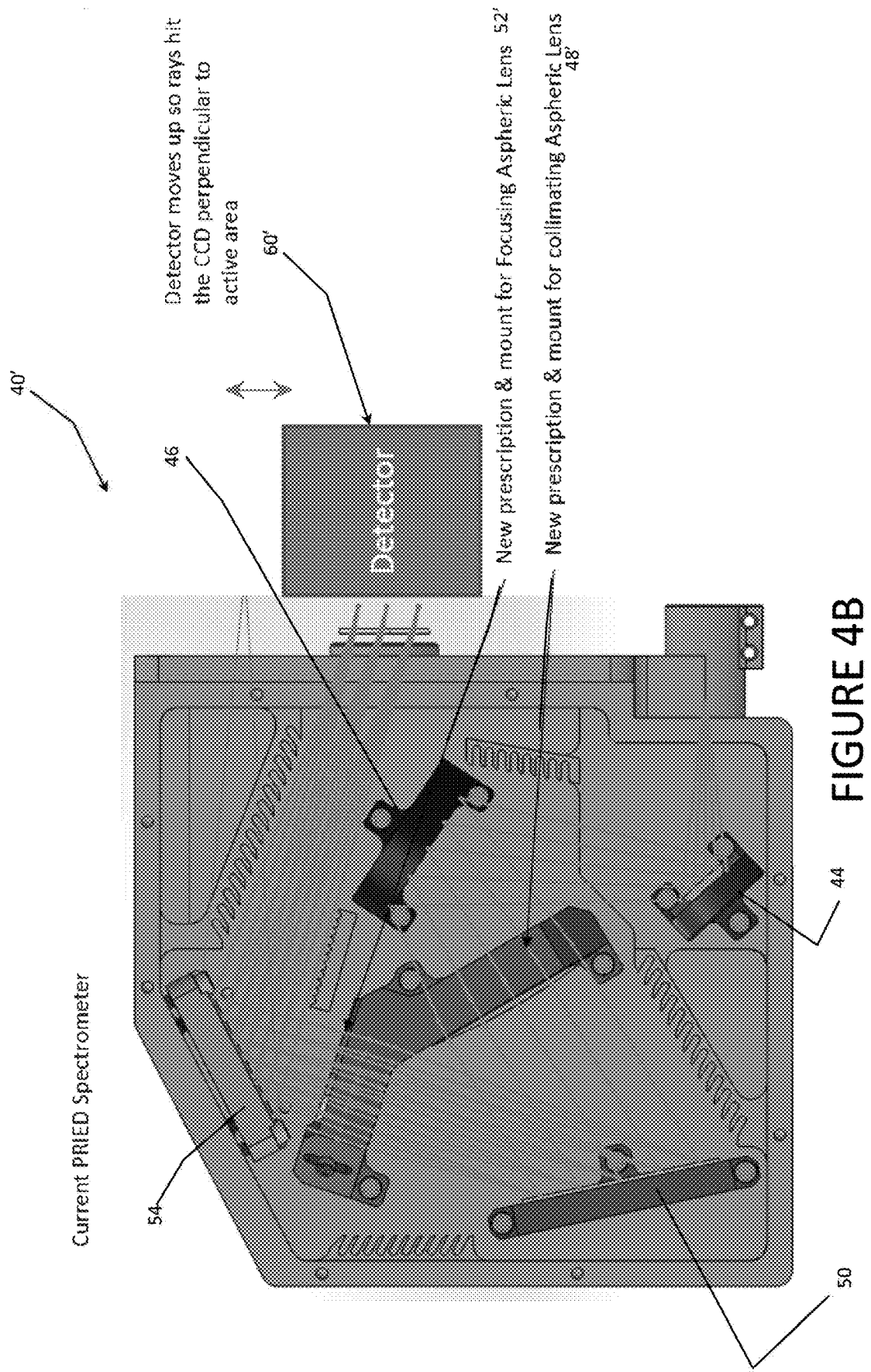

FIG. 4B is similar to FIG. 4A but shows variations of the spectrometer, namely an adjustable detector and a different arrangement of interior optical components.

Figure 5A:
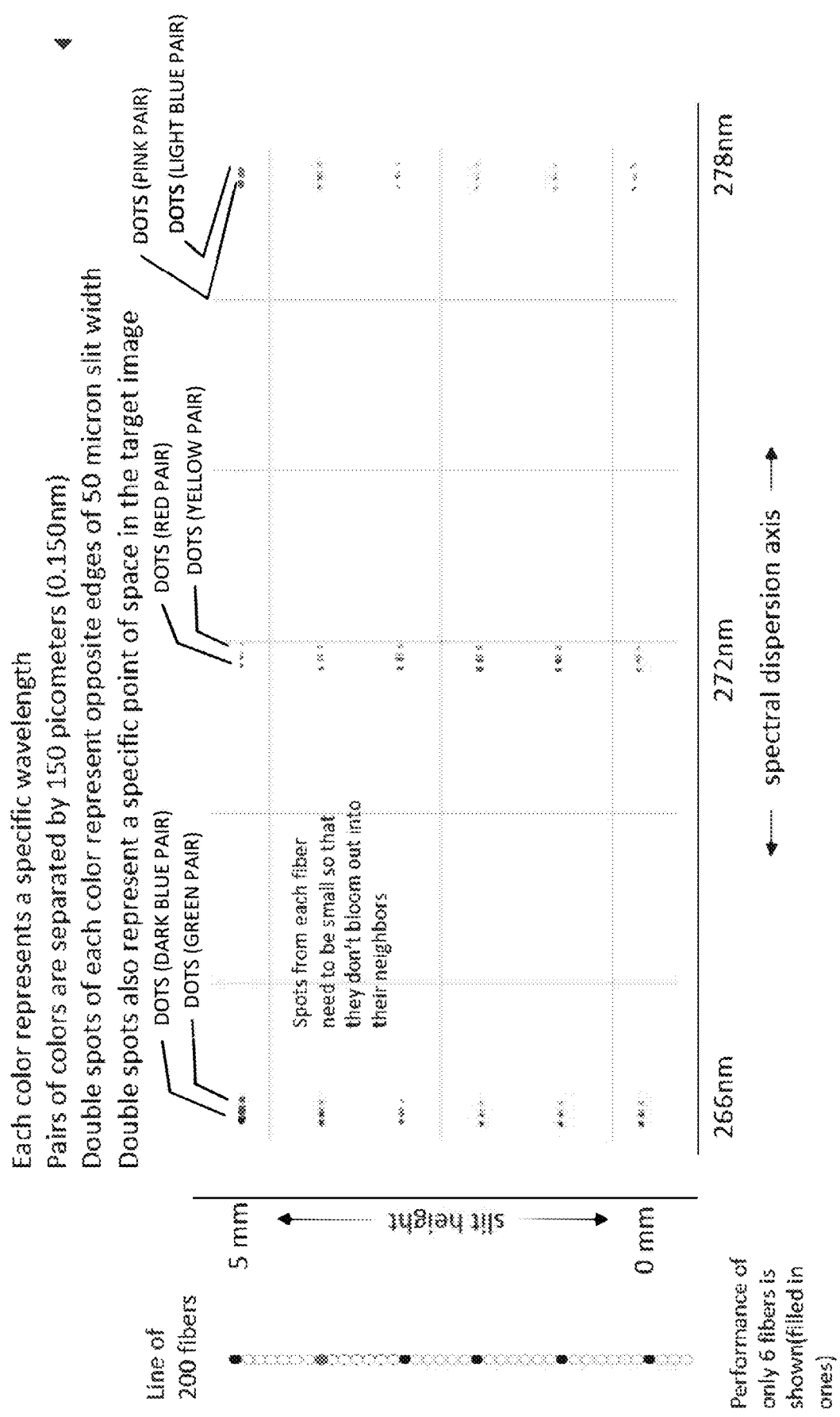
Figure 5B:
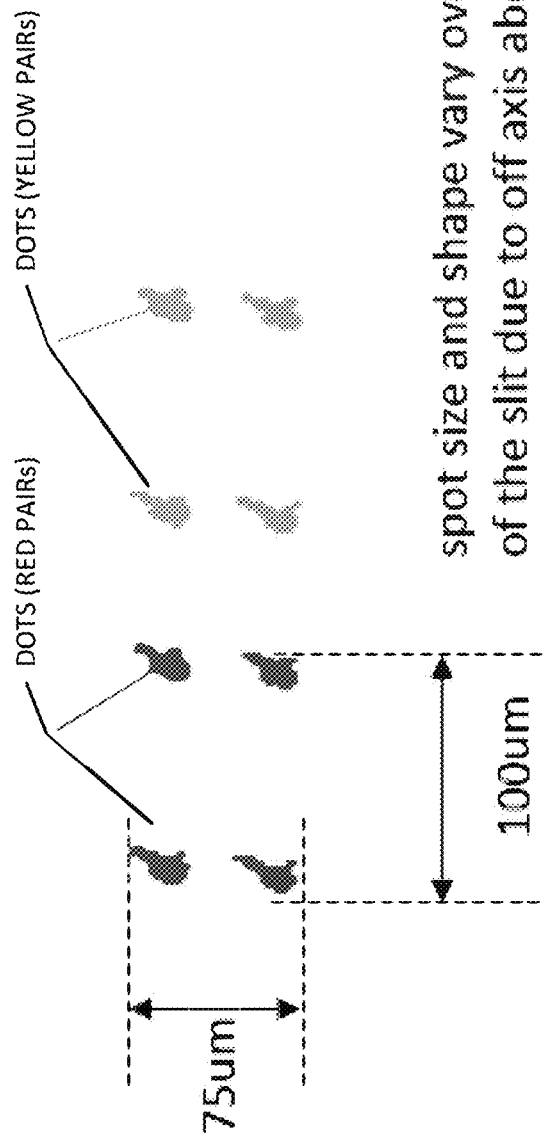
Figure 5C:
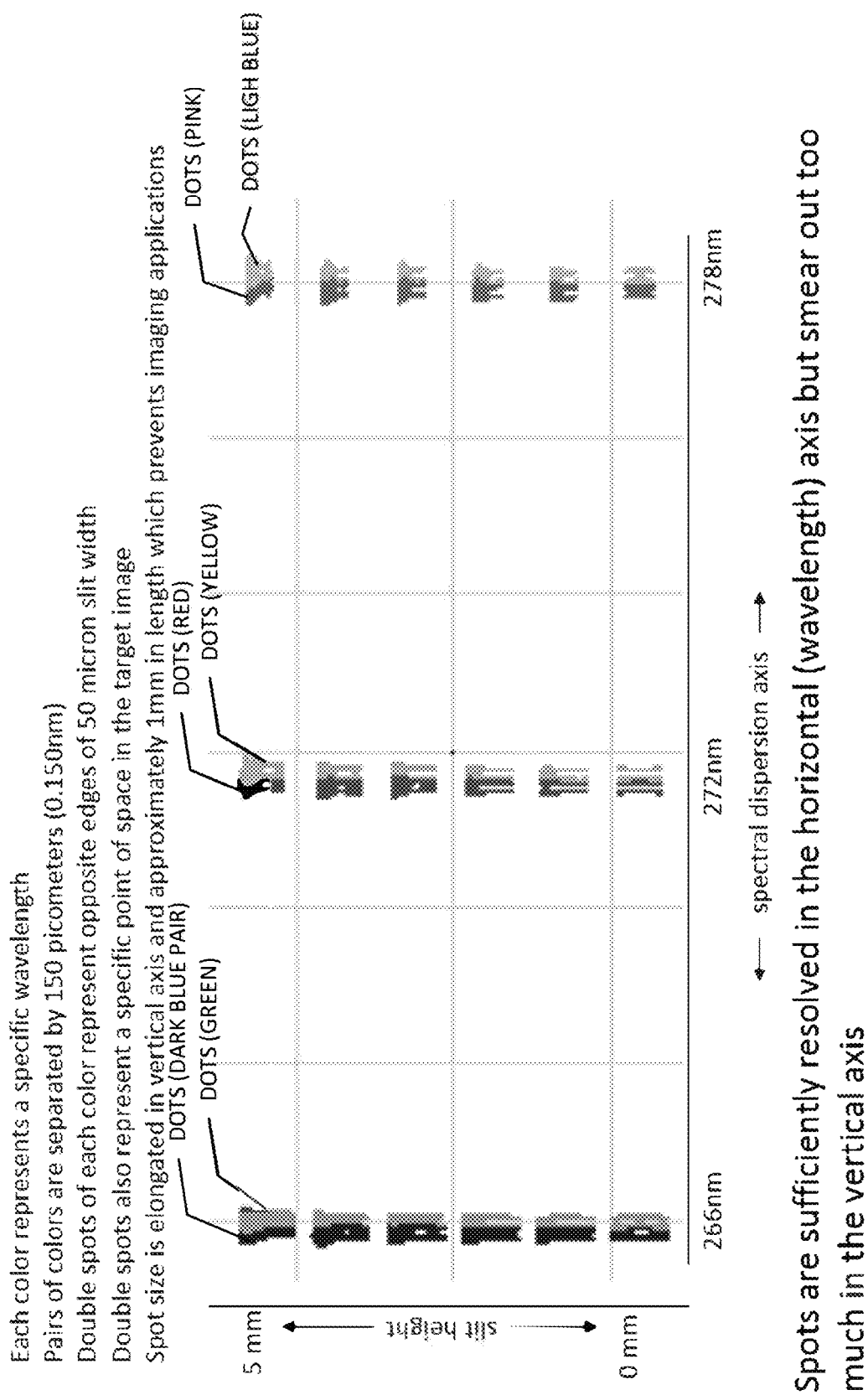
Figure 5D:
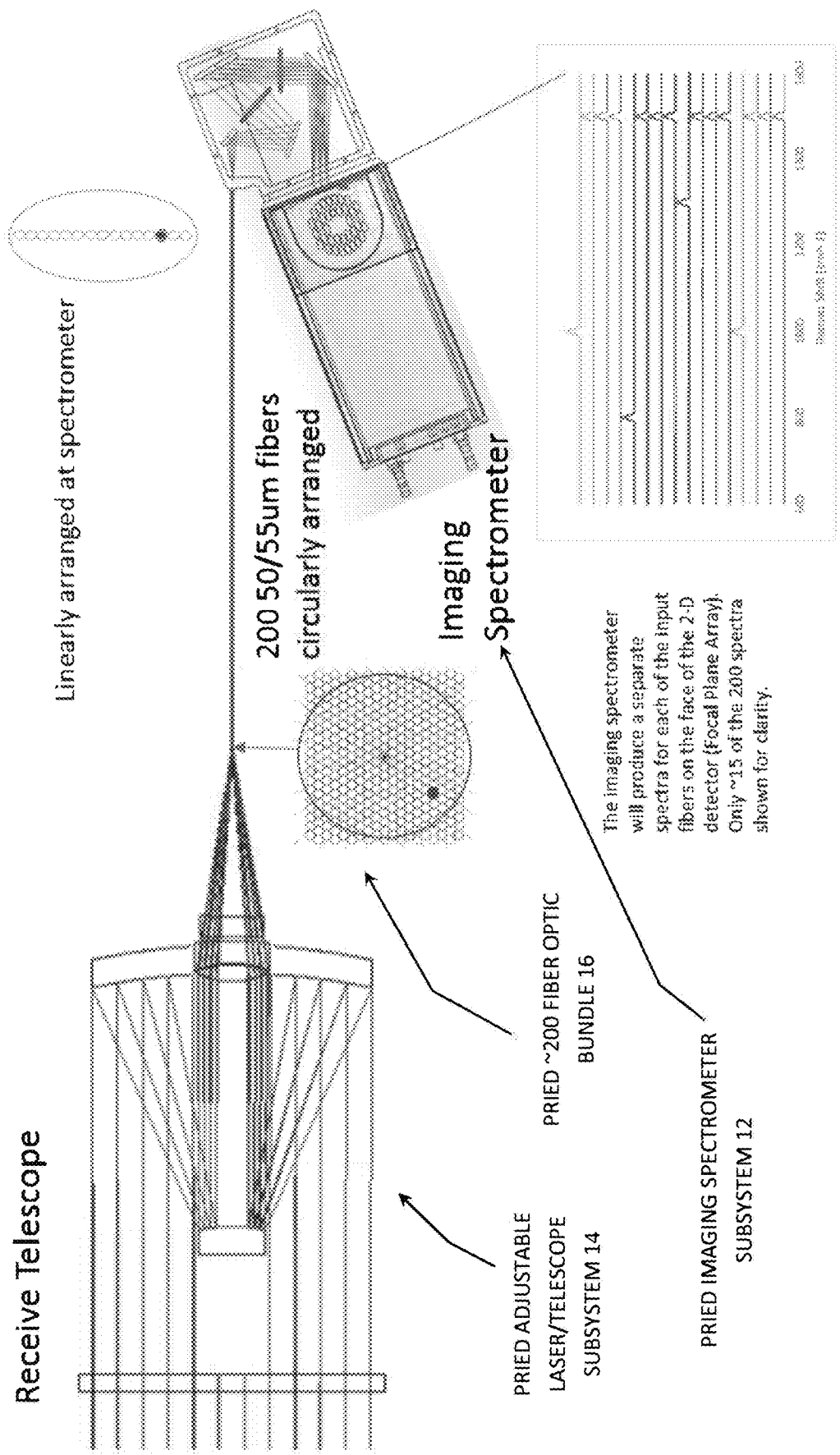

FIGS. 5A-D are: FIG. 5A is an optical model showing imaging performance of the spectrometer of FIG. 4A. FIG. 5B is a zoomed-in section showing 100 μm resolution of the imaging spectrometer of FIG. 4. FIG. 5C is an illustration of spot resolution related to FIGS. 5A and B. FIG. 5D is similar to FIG. 3 but diagrammatically illustrates further aspects of operating principles of PRIED.

Figure 6:
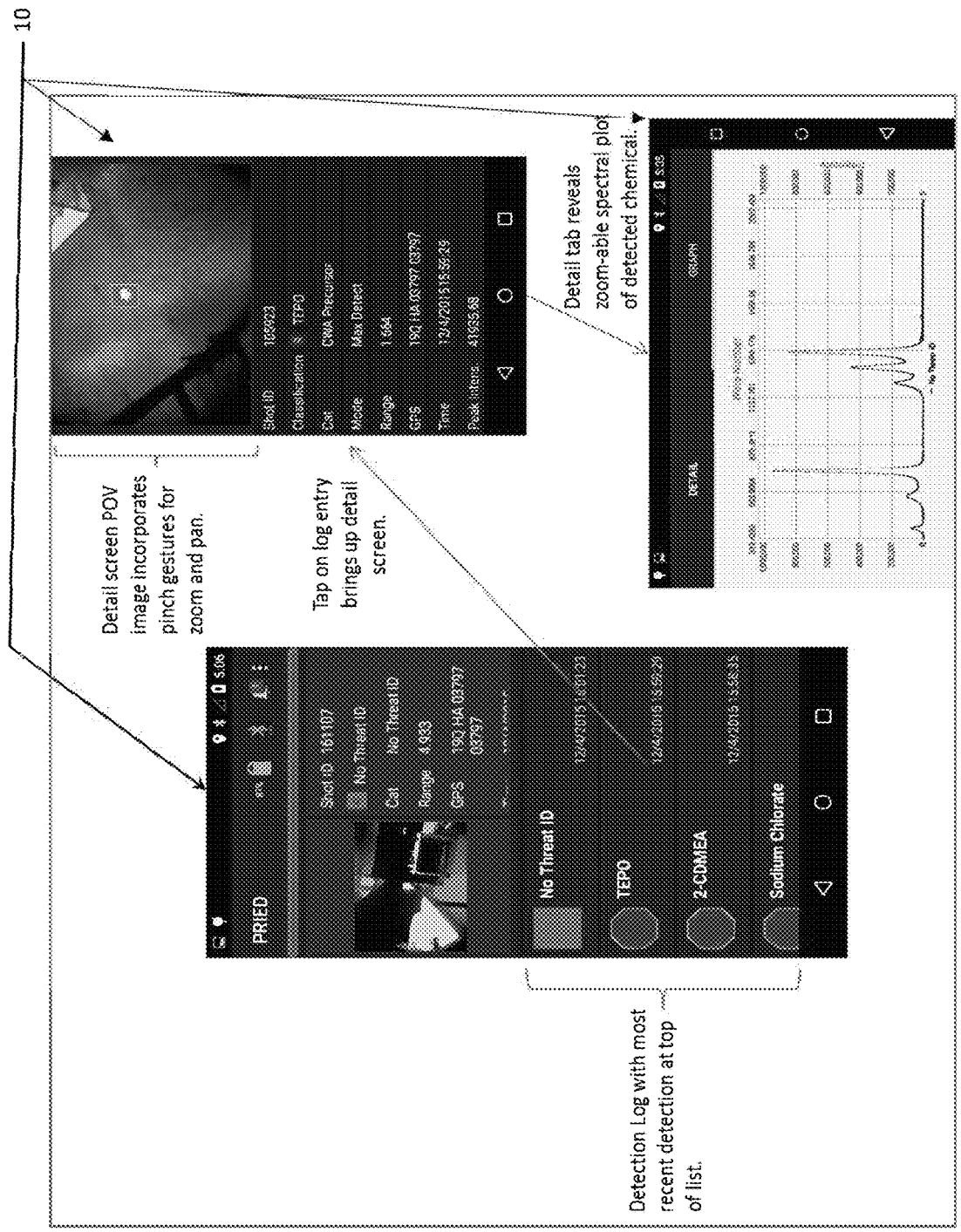

FIG. 6 is a PRIED User Interface App according to one exemplary embodiment of the invention.

Figure 7:
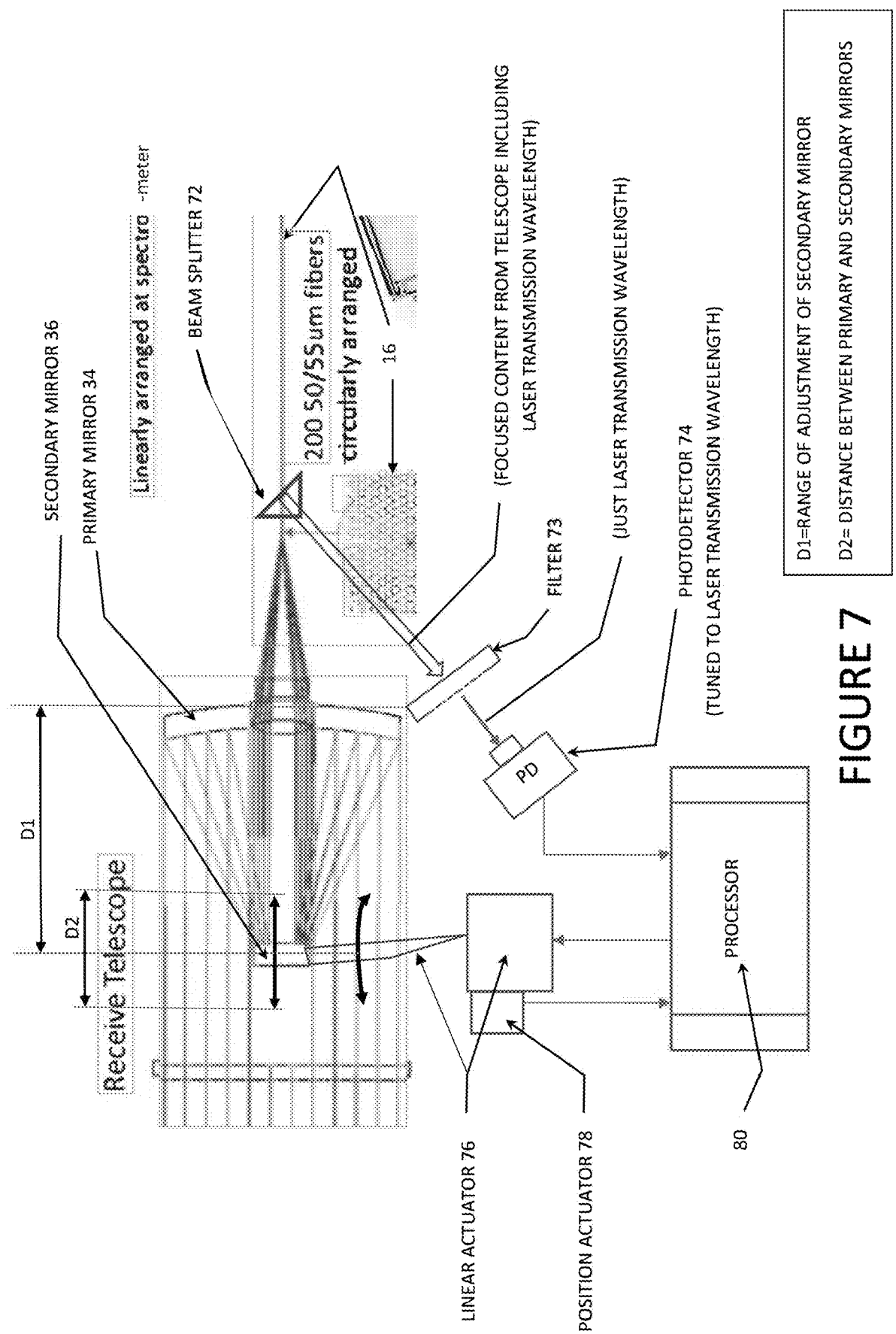

FIG. 7 is a highly diagrammatic illustration of an auto-focus/range estimation feature that can be optionally added to the configurations of FIGS. 1-6.

Figure 8:
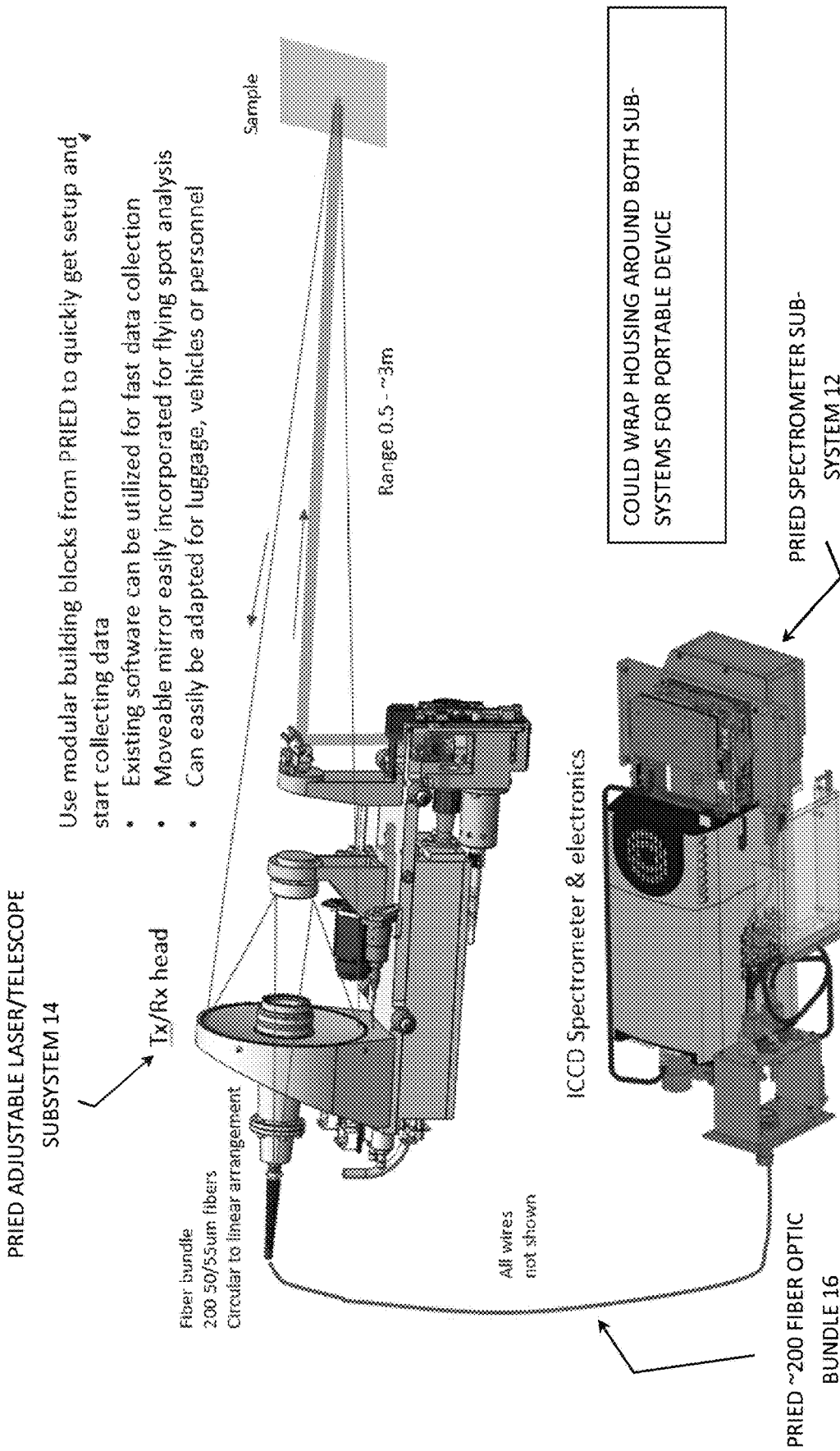

FIG. 8 is an illustration of a complete combination of laser/telescope sub-system, spectrometer sub-system, and fiber optic bundle connecting the two.

IV. DETAILED DESCRIPTION OF EXEMPLARY EMBODIMENTS OF THE INVENTION

A. Overview

For a better understanding of the invention, some examples of forms it can take all now be described in detail. It is to be understood these are neither exclusive nor inclusive of all such forms or embodiments the invention can take.

First, several embodiments and options useable with an imaging spectrometer and telescope associated with Raman spectroscopy for chemical detection at standoff distances will be described. Variations obvious to the skill you will be included within these embodiments.

Second, an expansion of those concepts to optional features or alternatives will be described. It will be understood by those skilled in the art that these are examples only for illustration and variations obvious to those skilled in the art of course possible.

It will also be understood that the examples focus, just for purposes of simplicity, on detection of a single chemical of interest or analyte AN. The concept of the invention can be applied to a wide variety of chemicals, chemical compounds, and chemical constituents, as is well known in Raman spectroscopy. Form factor and characteristics of the components, as well as the parameters to control them, will, of course, also vary according to need or desire.

B. System Elements

Figure 1:
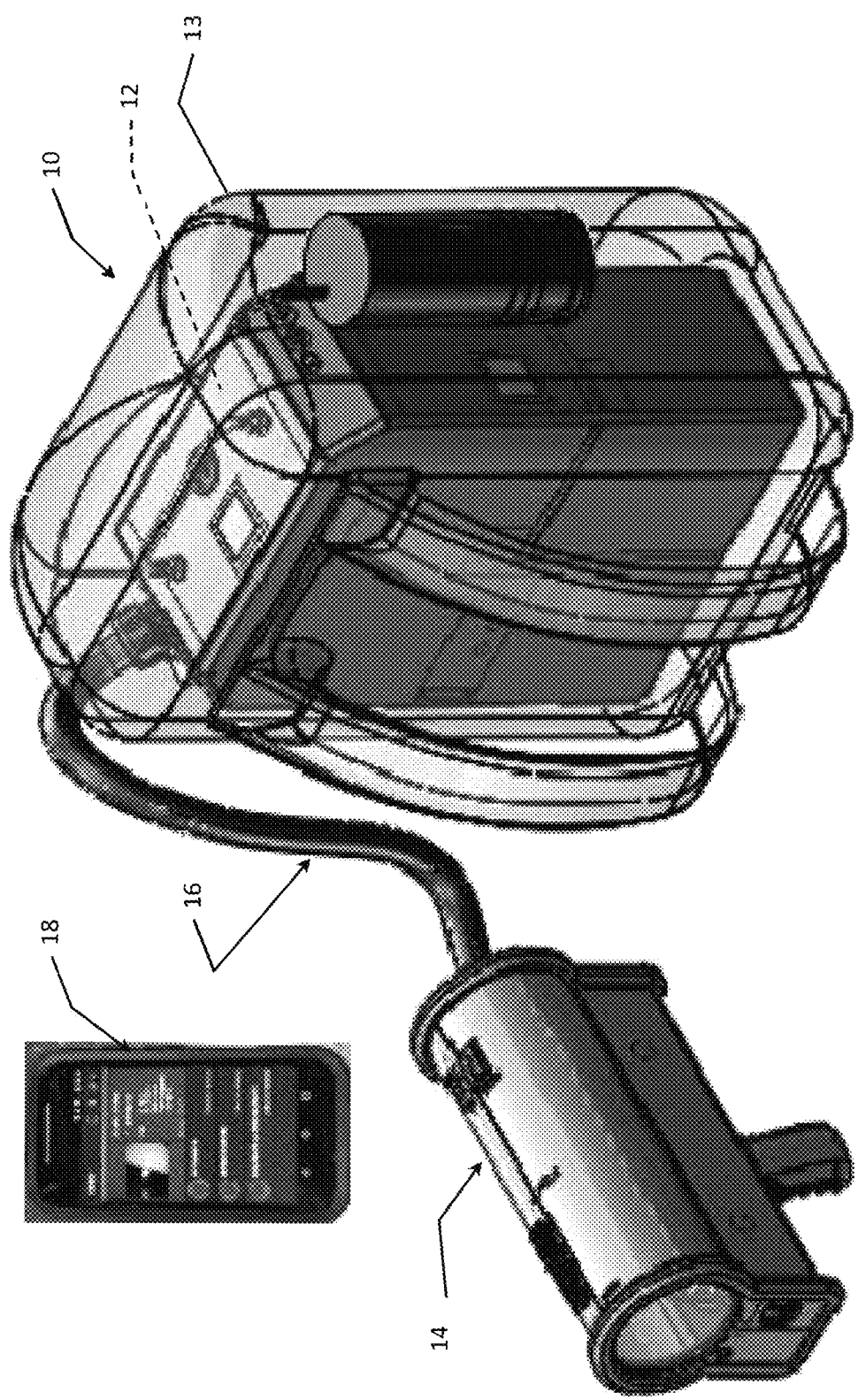
FIG. 1 is a model of PRIED with PDA (Android/iPhone) interface according to one exemplary embodiment of the present invention.

An overall system according the invention is illustrated at FIG. 1. System 10 includes an imaging spectrometer subsystem 12 of compact size that could be portably carried such as in a housing such as a backpack 13 with a battery source.

Optical interrogation or laser/telescope subsystem 14 includes a hand-held housing with a laser interrogation source (not shown) that can be aimed at the target object along an optical axis, and optical collection of reflectance returned along that optical axis. U.S. Pat. No. 8,125,627 and US Published Patent Application 2016/0103073 give examples of possible laser sources. US Published Patent Application 2016/0103073 gives examples and a system description of background information about how such subsystems generally operate. U.S. Pat. No. 8,125,627 gives additional background information but is for a much larger non-portable system. In general, any UV laser could be utilized.

Electrical power can be provided by a battery inside component 14 or from the battery in housing 13. An optical fiber bundle 16 connects the image plane of telescope 14 with an input to optical components of spectrometer 12. In this instance, bundle 16 includes on the order of 200 individual fiber-optics.

A digital device 18, including a display, provides a user interface. The display can be a touch screen to allow both viewing of information and entering of instructions. The different forms it could take includes smart watch, smart phone, tablet, head-mounted display, and night vision goggles, to name a few nonlimiting examples. It could also be wearable, for example in the sense of smart watches. It can provide both information on the display and tactile or haptic feedback (e.g. vibration or sound notifications).

The utilization of fiber-optic bundle 16 and a compact imaging spectrometer with the wirelessly communicated user interface 18 provides benefits in this technical field.

Examples of novel aspects for use with the system of FIG. 1 will follow.

All of the following ideas are implemented in a unit called the Portable Raman Improvised Explosive Detection System (PRIED).

C. System Embodiment

Figure 2:
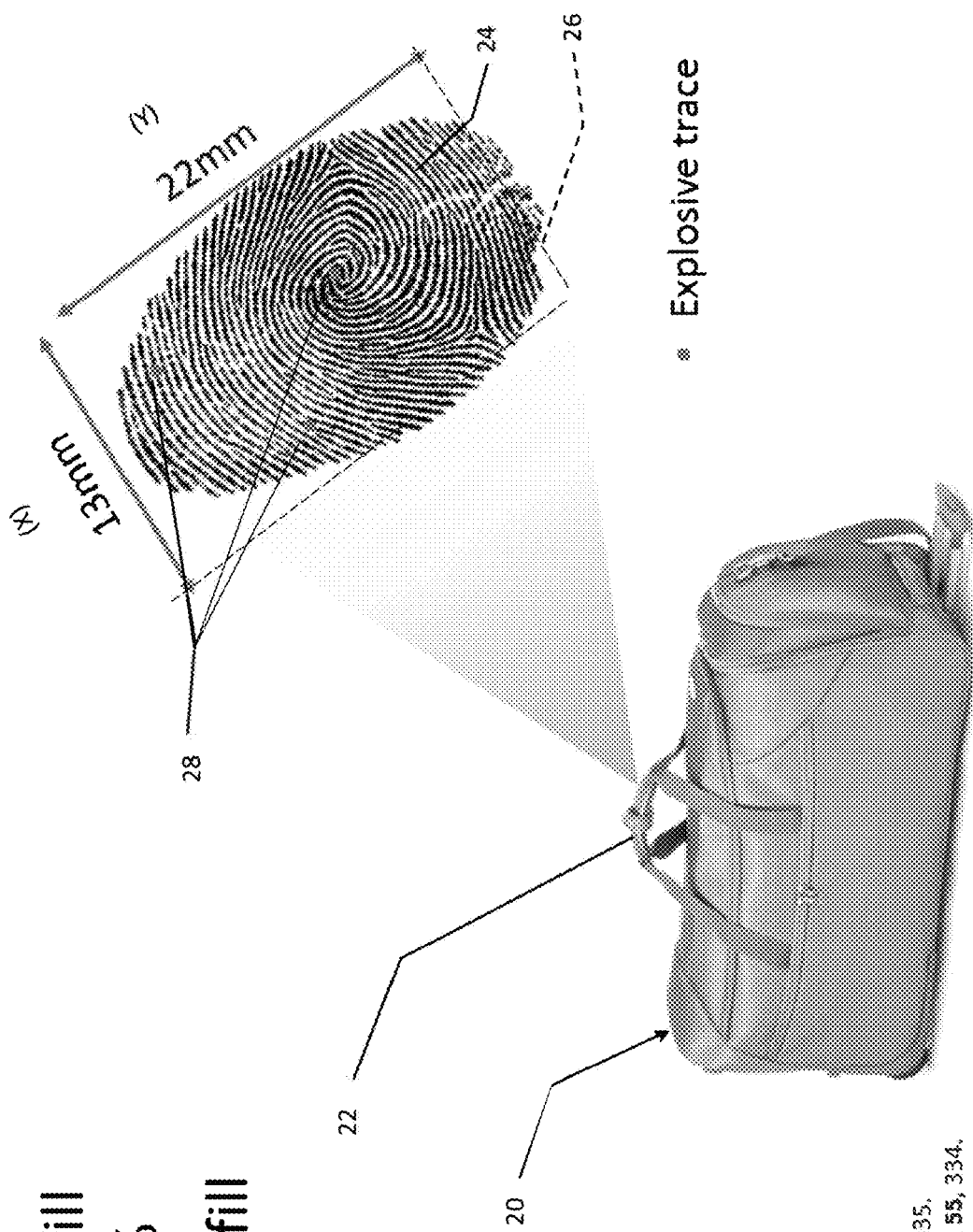
FIG. 2 is a typical example of an explosive finger print.

By particular reference to FIG. 2 and FIG. 3, a first specific embodiment of a system 10 according to aspects of the invention is shown and described.

1. Non-Spatial Raman Imaging for Fluorescence Rejection:

In order to achieve successful Raman detection, significant efforts must be made to minimize the fluorescence. Especially when the desired target is small amount of material on top of other substrates (e.g. trace amounts of explosive material on door handles, etc.). With this approach, a fiber array 16 consisting of multiple fibers $17_{1\text{-}n}$, (e.g. plural, tens, hundreds, or possibly more) is employed between the collection optics 30 and the spectrometer 40. Existing state-of-the-art ideas focus on utilizing the multiple fibers and mapping the fibers location so that spatial data analysis can be performed thereby enhancing the detection performance. A unique feature in this invention is that the data is analyzed fiber 17 by fiber 17 for Raman detection events and no spatial information is utilized. With this approach, the trace amounts of material (see FIG. 2 at ref. no. 28) actually block some amount of the background material which typically is fairly fluorescent. FIG. 2 and FIG. 3 show a concept of the equipment diagram and the fluorescence reduction (FIG. 3), as well as part of the conceptual foundation for the technique (FIG. 2). See Verkouteren. J. Forensic Sci. *Particle characteristics of trace high explosives: RDX and PSTN.* 52(2), 335-340 (Mar. 2007) and Verkouteren, et al. *Automated mapping of explosives particles in composition C-4 fingerprints.* J. Forensic Sci. 55(2), 334-340 (Mar. 1, 2010), both incorporated by reference herein. The spectral data shows the comparison between two individual fibers 17 (of the fiber array 16). It can be seen that in fiber 1, the desired signal of interest from and small amount of explosive is greater than that of fiber 2. Additionally, the fluorescence signal in fiber 1 (the amount of signal in the 1500-3000 $cm^{-1}$ band) is reduced cause the trace amounts of explosive are blocking the fluorescence.

D. Spectrometer Embodiment

A specific spectrometer that can be used in the system of FIG. 1 and FIG. 3 is now described.

2. Novel Imaging Spectrometer for UV Raman

Most imaging spectrometers are big (1 cu. ft.), whereas the PRIED contains a small compact custom designed imaging spectrometer. FIG. 4A provides and overview of an imaging spectrometer 40 with features according to aspects of the invention. It utilizes a linear array 16B of fibers $17_{1\text{-}197}$ as an input (see 42 and 44) (197 50 µm core diameter fibers), which is collimated by an aspherical lens 48. The output $45_{1\text{-}197}$ of this lens 48 hits a holographic grating 50 (4320 l/mm) which diffracts the light. This light $51_{1\text{-}197}$ is focused by another aspheric lens 52 onto the detection plane 61 of a 2D CCD array 60. The unique features of this imaging spectrometer are that imaging performance (spot size at the CCD) is 100 µm in size from each of the 50 µm fibers (see FIGS. 5A-D).

FIG. 4B illustrates a spectrometer 40' similar to spectrometer 40 of FIG. 4A with variations indicated in annotations on FIG. 4B.

A linear arrangement of fiber optic bundle 16B at the input to the spectrometer is the easiest and most common to implement. This system will work for any amount of sample but presently it is believed to work best for trace amounts.

FIGS. 5A-D provide an overview where by each of the 200 linear fibers will produce a total separate spectrum on the input face of the 2-D detector (in a non-imaging spectrometer these spectra would be smeared together and not separate). The software reads out the image from the 2-D detector and then separates them into the correct number of individual spectra. FIGS. 5A and B show the performance of the imaging spectrometer to ensure that the spots are small and separated. The annotations to each of FIGS. 5A-D provide further details of the principles illustrated.

a. Each color represents a specific wavelength.
b. Pairs of colors are separated by 150 picometers (0.150 nm).
c. Double spots of each color represent opposite edges of 50 micron slit width. Double spots also represent a specific point of space in the target image.
d. Colors represent 2 different wavelengths separated by 150 pm 4 points for each wavelength represent point sources at corners of a specific location along a 50 µm slit.
e. Spot size and shape vary over the length of the slit due to off axis aberrations but are kept low by a combination of lens shape optimization and alignment bias.

FIGS. 5A-D are intended to illustrate how the system is set up provide individual spectral information from each optical fiber 17. In FIG. 5A, diffracted output from six of the 197 fibers $17_{1\text{-}197}$ are modeled at three different dispersion wavelengths. This demonstrates how spectral content at each of those individual six fibers can be imaged and, thus, individually analyzed for spectral content, including Raman content. FIG. 5B shows in enlarged scale how dispersed content (e.g. for 272 nm in FIG. 5A) can be imaged at the image plane of the digital imagers and distinguished for spectroscopic analysis. This highlights the subtle but important innovation according to the invention. FIGS. 5C and D provide further details about operating principles. That design of an imaging spectrometer for detection of trace amounts of chemical of interest, makes the assumption that a trace amount (on the order of size of the size of output of one optic fiber at the image plane of the digital imager) would mask what would otherwise by high fluorescence content form the underlying surface (e.g. other parts of a fingerprint or the bag handle in FIG. 2). Thus, if the spectral content of one fiber "lights up" for a wavelength of a molecular species of interest know to correlate with an explosive, for example, is confirmed as detection of that trace amount. The FOV, so to speak, of the fiber at the imaging plane is assumed to basically be only the trace chemical (and not just fingerprint or bag handle, e.g.). Thus, a strong amplitude at the wavelength of interest (e.g. AN: 1040 cm$^{-1}$ in FIG. 3 graph of signals), is considered "lighting up" the detection of AN. There is neither a requirement to know where on the handle or use fluorescence removal processing overhead.

Thus, implementation of a 197 fiber optic bundle would result in 197 spectral images (as per FIG. 5A), one for each fiber, each of which can be individually analyzed for whether or not it has "lit up" regarding a specific wavelength or wavelengths of interest.

It may well be that more than one fiber "lights up" in the sense an evaluation of the signal at that fiber meets criteria indicative of the presence of the molecular species of interest. If a few "light up" it can mean several traces have been detected in the same FOV. If many "light up" it can mean that the chemical of interest has been detected in a larger amount (e.g. larger area than a trace) on the handle. But one important aspect of the invention is the ability to detect trace amounts, and without the need for spatially mapping of optical fibers in the bundle, and without relying on fluorescence removal techniques.

E. User Interface Embodiment

A specific user interface 18 that can be used in the system of FIG. 1 and FIG. 3 is now described, including in conjunction with FIG. 6.

3. Novel Operator Feedback for a Chemical Sensor:

PRIED includes more intuitive feedback mechanisms for chemical sensor operation via wearable technology than any other chemical sensor on the market. Currently the PRIED sensor 13/14 provides feedback to the operator wirelessly (such as Bluetooth or Wi-Fi) via an app that resides on a mobile device 18 such as an Android phone, iPhone, or tablet (like an iPad.) In one form, the device 18 can be tethered to the operator with an arm-band so that it is wearable and is separate from our chemical sensor system 13/14. The wearable device app provides specific detection events in a visible log file that includes a photograph of the field of view from the sensor 14 point of view. It also has details presented in the application such as the spectral plot of the detected chemical. This is unique and different from current state-of-the-art systems such as Smiths Detection System's Ace-ID™ (from Smiths Detection Americas, Edgewood, Md. (USA) and ThermoFisher (from ThermoFisher Scientific, Waltham, Mass. (USA)).

Scientific's First Defender™ products an operator interface and feedback built into the device. Unique features of operator feedback via device 18 according to the present invention are as follows:

a. Wireless connection to operator interface
b. Configuration of the sensor setup via the wireless remote app
c. Log file of detection events with simple red/green threat/no-threat indication
d. Photograph of the detection area providing context to the operator with pinch gesture zoom in details view
e. Spectral plot of the detected chemical
f. Overlay of spectral plot with the reference spectrum g. GPS data-stamp for location and time of the detection event (using on-board GPS or other geospatial sensors of device 18)

h. Range of the detected threat from the operator

Additional possible features with device 18 include the following:

Vibration alerts triggered by detection events from the PRIED, provide a haptic type feedback to the operator. As the laser of 14 is scanned across a surface (e.g. carrying strap 22 of luggage bag 20 of FIG. 2), a detection event triggers a vibration in the wearable device 18 (such as an iPhone, Apple Watch, Android Watch, or tablet.) This vibration provides near-real-time feedback to the operator that an area of interest has been encountered without having to look at the visible alerts pushed to the interface 18A (see FIG. 6) of tablet, phone, or watch. This near real time, haptic signaling provides a covert, "Geiger Counter," type signaling to the operator without the need for audible or visible alerts. This is different from commercially-available Ace-ID™ (Smiths Detection Americas), Target-ID™ (Smiths Detection Americas), FirstDefender RM™ (ThermoFisher Scientific), and FirstDefender RMX™ (ThermoFisher Scientific) detection systems that only provide built-in visible and audible alerts.

The detection events can also be presented to the operator via wearable technology such as Google Glass. The detection log file, spectral information, and sensor POV (the user's Point of View) camera information can be overlaid onto the field-of-view (FOV) to provide detection results within the context of the operator's FOV from the wearable display 18A. This is unique and is also not found on competitor's products such as the Ace-ID™, Target-ID™, FirstDefender RM™, and FirstDefender RMX™ detection systems that only provide built-in visible and audible alerts.

Haptic feedback and remote wireless display technology can be combined to provide detection information to operators using night vision goggles. The remote display and haptic feedback avoid the blooming and image saturation caused by other sensors with built-in display systems.

As will be appreciated, the features described here regarding a user interface and control can be applied in different contexts, including to other than an imaging Raman spectrometer, in analogous ways.

F. Auto-Focus/Range Finder Embodiments

A specific auto-focus potential feature that can be used in the system of FIG. 1 and FIG. 3 is now described. See also FIG. 7. It can include a range-to-target sub-feature.

4. Novel Auto-Focus/Range Estimator:

A closed loop focusing mechanism 70 (FIG. 7) could be implemented by optimizing the return signal 31 (see also FIG. 3) from the diffuse reflection from the target. Because PRIED preserves an image of the laser spot and the 262 nm laser transmission line needs to be rejected from the spectrometer, this rejected light could be used to optimize the focus of the telescope. In this scheme, the filter optic would be used to split (e.g. beam splitter 72, FIG. 7) the returned 262 nm light from the target (e.g. by band pass filter 73 and re image it onto a single element photo-detector 74. The secondary motion mechanism 76 (e.g. linear or other actuator) could be dithered (adjusted incrementally in either direction in the range $D_1$ of FIG. 7) until the return signal passes through maxima at which point the position of the primary telescope lens 34 and secondary telescope lens 36 would be at their optimal focus. Using a mechanical position resolver 78 for the secondary mirror 36, the distance to target could then be estimated based upon the spacing $D_2$ between the primary and secondary mirrors. An aperture sized to approximately that of the optimized spot would be placed in front of the photo-detector 74 to guarantee a fall off of signal strength as the image becomes defocused. Alternatively, a photo-detector with active area about the size of the reimaged laser spot could also be used. The focus algorithm (operating on conjunction with a processor or controller 80) would be required to:

a. Move the mirror 36 in a direction b. If the signal increases, continue to move in the same direction c. If the signal decreases, reverse direction d. Continue iterating until the change in signals strength drops below some acceptable delta that will most likely be range dependent (the hysteresis band will be a function of the relative position between the mirrors)

This concept is unique from other focus mechanisms because it uses the transmitted laser light from the sensor 30 to set the focus position of the detection system. It does not rely on a secondary range-finder or contrast focus algorithm to determine the relative position of the primary and secondary mirror to set the focus.

Thus, as can be appreciated by reference to FIGS. 2 and 3, a subtle but important insight is use of a bundle of many individual fiber-optic cables. First ends of the fibers in the bundle are formed into a 2-D pattern at the output or imaging plane of the focusing telescope. Thus, the image from the field of view of the telescope is essentially imaged onto the 2-D pattern of plural fibers. The individual fibers are the analogue of a 2-D array of pixels in a digital imager. As illustrated FIG. 2, if the target surface is handle 22 of luggage bag 10 on airport floor, the interrogation laser of telescope 14 can be scanned across handle 22 looking for fingerprints that may include minute (micro-scale) traces of explosives 28. Fingerprint 24 has a general width X and length Y in a 2-D plane. The collection of reflectance, including both an image of that X-Y area in the visible light spectrum plus the return of reflectance of the interrogating laser at its transmission wavelength is collected at telescope 30. See FIG. 3.

As indicated diagrammatically at FIG. 3, telescope 30 can optically manipulate the received reflectance as follows:

a. A collimator 32 can collimate the field of view received light (illustrated diagrammatically by light rays 31).

b. A primary mirror or lens 34 can converge the collimated light (rays 33) to secondary mirror 36 (rays 35).

One end of fiber-optic bundle 16, here approximately 200 fibers circularly arranged in pattern 16A of FIG. 3, is aligned with the optical axis of telescope 30. As illustrated in FIG. 3, minute explosive traces 28 in a fingerprint 24 on handle 22 of bag 20 (FIG. 2), can be correlated in spatial position to the circular arrangement 16A of fiber-optic bundle 16. The subtle discovery is that such particles 28 effectively mask or at least diminish what otherwise could be fluorescence from those locations caused by the laser. As illustrated in FIG. 3, by comparison of the signals through a fiber-optic associated with an explosive trace 28 in the telescope field of view with a fiber-optic associated with an area other than an explosive trace 28, any offset of signal intensity at certain wavelengths can be detected. It is assumed such a significant offset is related to presence of a masking by trace 28 of what otherwise would be heavily influenced (and more difficult to detect) by fluorescence. That output from that fiber-optic 17 with that detected offset can then be evaluated for presence of a chemical of interest such as an explosive.

FIG. 4 illustrates that the circular pattern at 16A is rearranged at output end 16B of bundle 16 into a linear pattern. This linear array 16B would be routed to fiber input 42 of housing 41 of imaging spectrometer 40. Component 44 would direct the outputs $45_{1-197}$ of each fiber $17_{1-197}$ of the linear array 16A to component 46. Component 46 would emit the content (indicated diagrammatically at $47_{1-197}$) of each fiber-optic through collimating lens 48. Grating 50 would receive the collimated output $49_{1-197}$ of each fiber-optic to diffraction grating 50 (diffracted output related to each fiber shown diagrammatically at $51_{1-197}$). Mirror 54 would focus all of those the diffractions (diagrammatically indicated at $55_{1-197}$ to housing 41 output 56, which is aligned with detector plane 61 of a CCD imager 60. Detector plane 61 would therefore receive essentially diffractions ($57_{1-197}$) related to each fiber $17_{1-197}$ (see FIGS. 5A and B) but in a linear array. Thus, the diffracted content of each fiber can be resolved relative to other fibers and a signal (see e.g. FIG. 3) related to each fiber $17_{1-197}$ derived from the images at detection plane 61. Software can then evaluate each signal and compare any two signals to identify those signals indicative of the presence of a trace 48. Software to evaluate the diffracted content can be similar to that used for other Raman spectroscopy image evaluations systems. The difference is that at least two selected signals related to the diffracted content of different individual optical fibers out of the composite bundle of fibers $17_{1-197}$ are compared to attempt to reveal offsets at specific wavelengths of interest (e.g. those related to analytes of interest AN) that are indicative of the masking effect, as explained above in the two-signal comparison regarding FIG. 3.

FIGS. 5A and 5B illustrates how the arrangement produces performance outcomes from the system for content at the CCD imager.

FIG. 6 illustrates a few nonlimiting examples of what type of information could be displayed on display 18A of user interface 18. Variations obvious to those skilled in the art are of course possible.

FIG. 7 is a high-level schematic of focusing telescope 30 with primary and secondary lenses. Actuator 76 can be any of a number of electrically-controlled movement actuators commercially available yet in compact form factor for the portable system 10 of these examples. Beam splitter 72, filter 73, photodetector 74, and position resolver 78 can also be off-the-shelf components such as are known to those skilled in the art.

FIG. 8 is an illustration of a complete system including laser/telescope sub-system 12, spectrometer sub-system 14, and fiber optic bundle 16. As indicated, the sub-systems could be housed in a portable housing (either individually like FIG. 1 or perhaps all together in one integrated housing).

G. Options and Alternatives

As will be appreciated by those having skill in this technical art, options and alternatives to the foregoing exemplary embodiments are of course possible. Variations obvious to those skill to be included within the invention which is not limited by the embodiments disclosed herein. Some additional examples of options and alternatives are as follows.

Form Factor

As indicated above, the form factor of each of the components can vary according to need or desire. Portability can be approximately less than a fraction of a meter in all dimensions for housing 13 in FIG. 1, the same for hand-held telescope 14 in FIG. 1, and the same for user interface 18.

Wireless communication and length of fiber bundle 16 can be varied according to need or desire.

Control System

Components necessary to allow inter-communication between electrical/electronic functions of the system (e.g. the application running on wireless smart phone 18, the on/off control of the laser in 14, the on-off and processing associated with the spectrometer, and the components of FIG. 7 (if used)), can be selected and configured in a variety of ways according to the designer's needs and desires. This could include some type of programmable processor or controller.

Adjustability

Both factory settings and subsequent adjustments of operation of the system can be easily accomplished by programming and programming of a microprocessor or other intelligent control, including any number of factors, parameters, and the like according to the designer's need or desire. Such programming is well-known.

What is claimed is:

1. An apparatus for use in sensing presence of chemicals or chemical compounds from a standoff distance comprising:
    a. a portable housing containing:
        i. an imaging spectrometer;
        ii. an electrical power source;
    b. a portable light source and receiver comprising:
        i. a collimated illumination source adapted to direct light energy of predetermined interrogation transmission wavelength along an optical axis to a target surface at standoff distances;
        ii. an optical receiver having a field of view adapted to collect light energy, including reflectance from the illuminated target surface, along the optical axis;
    c. an optical connection between the optical receiver and the imaging spectrometer comprising:
        i. a bundle of a plurality of individual optical fibers having input ends and output ends;
        ii. the input ends generally circularly arranged a plane transverse to the optical axis and the collected light energy of the optical receiver, each optical fiber roughly carrying a portion of the collected reflectance that is spatially related to the field of view of the optical receiver;
        iii. the output ends arranged in a linear array, such that each output end transmits its portion of the field of view of the optical receiver to the imaging spectrometer;
    d. a portable user interface comprising:
        i. a communication connection to the imaging spectrometer;
        ii. a display adapted to present or generate information relevant to sensing presence of chemicals or chemical compounds by the imaging spectrometer;
    e. wherein the imaging spectrometer comprises:
        i. a fiber optic input to receive transmitted light from the linear array at the output ends of the fiber optic bundle;
        ii. a collimator;
        iii. a holographic grating which diffracts the light from the collimator;
        iv. a focusing lens to focus the diffracted light to a 2D detection plane comprising an array of pixels of a digital imager;
        v. whereby such components are configured to achieve;

(1) an imaging performance comprising a spot size at the image plane on the order of 100 μm in diameter; but
(2) in a centimeter scale housing instead of tens of centimeter scale.

2. The apparatus of claim 1 wherein the chemicals or chemical compounds comprise explosives and the standoff distance comprises meters to hundreds of meters.

3. The apparatus of claim 1 wherein:
a. the portable housing is back-pack sized;
b. the portable light source and receiver is hand-held size;
c. the power source comprises a battery;
d. the optical connection comprises tens to hundreds of optical fibers of centimeters to meters in length;
e. the user interface comprises a handheld or wearable digital device including but not limited to a smart phone, smart watch, tablet, optical head-mounted display (glasses), night vision or other goggles.

4. The apparatus of claim 1 wherein the optical light source and receiver comprises:
a. a laser light source;
b. a telescope receiver comprising:
i. collection optics to receive light and focus the received light to the circular array of input ends of optic fibers roughly spatially correlated to the field of view of the telescope so that each optical fiber represents a significant portion of the field of view of the telescope.

5. The apparatus of claim 1 wherein the user interface comprises;
a. a digital processor;
b. an on-board digital memory;
c. an application comprising one or more features comprising:
i. user controls;
ii. wireless communication;
iii. selectable views on the display comprising one or more of:
1. field of view of the telescope from the image plane of the imaging detector;
2. spectral plot(s) of selected portions of the field of view;
3. photograph of the field of view;
4. detection event indicators;
5. GPS location and time stamp for a detection event;
6. range from target surface related to a detection event.

6. The apparatus of claim 5 wherein the user controls include:
a. configuration of operating parameters of the imaging spectrometer;
b. selection between selectable views;
c. selection of present and stored detectable events and information about each.

7. A system comprising the apparatus of claim 1; and one or more of
a. the imaging spectrometer comprising:
i. a fiber optic input to receive transmitted light from the linear array at the output ends of the fiber optic bundle;
ii. the collimator;
iii. the holographic grating which diffracts the light from the collimator;
iv. the focusing lens to focus the diffracted light to a 2D detection plane comprising an array of pixels of a digital imager;
v. whereby such components are configured to achieve:
1. an imaging performance comprising a spot size at the image plane on the order of 100 μm in diameter; but;
2. in a centimeter scale housing instead of tens of centimeter scale;
b. the user interface comprising:
i. digital processor;
ii. an on-board digital memory;
iii. an application comprising one or more features comprising:
1. user controls;
2. wireless communication;
3. selectable views on the display comprising one or more of:
a. field of view of the telescope from the image plane of the imaging detector;
b. spectral plot(s) of selected portions of the field of view;
c. photograph of the field of view;
d. detection event indicators;
e. GPS location and time stamp for a detection event;
f. range from target surface related to a detection event; and
c. the telescope comprising:
i. a primary mirror and a secondary mirror along a telescope optical axis to focus collected light based on distance between the primary and secondary mirror, the collected light including an image of reflectance from the target surface of the interrogation beam at its transmission wavelength;
ii. an optical splitter along the optical axis after the primary and secondary mirrors to split received collected light into two paths:
1. one path directed to the input ends of the fiber optic bundle for the imaging spectrometer;
2. the other path directed to a photo-detector sensitive to the transmission wavelength of the interrogation beam collected from the target surface;
iii. an actuator in operative connection to at least one of the primary and secondary mirrors operatively connected to the photodetector to automatically adjust primary to secondary mirror distance based on measured intensity of the transmission wavelength of the interrogation beam to automatically focus the telescope.

8. The system of claim 7 further comprising a position resolver in the telescope calibrated to estimate distance to the target surface based on sensed distance between the primary and secondary mirrors when automatically focused.

9. An apparatus for use in sensing presence of chemicals or chemical compounds from a standoff distance comprising:
a. a portable housings containing:
i. an imaging spectrometer;
ii. electrical power source;
b. a portable light source and receiver comprising:
i. a collimated illumination source adapted to direct light energy of predetermined interrogation transmission wavelength along an optical axis to a target surface standoff distances;
ii. an optical receiver having a field of view adapted to collect light energy, including reflectance from the illuminated target surface, along the optical axis;
c. an optical connection between the optical receiver and the imaging spectrometer comprising:

i. a bundle of a plurality of individual optical fibers having input ends and output ends;
ii. the input ends generally circularly arranged in a plane transverse to the optical axis and the collected light energy of the optical receiver, each optical fiber roughly carrying a portion of the collected reflectance that is spatially related to the field of view of the optical receiver;
iii. the output ends arranged in a linear array, such that each output end transmits its portion of the field of view of the optical receiver toile imaging spectrometer;
d. a portable user interface comprising:
i. a communication connection to the imaging spectrometer;
ii. a display adapted to present or generate information relevant to sensing presence of chemicals or chemical compounds by the imagining spectrometer;
e. wherein the illumination source and optical receiver further comprises:
i. a primary mirror and a secondary mirror comprising a telescope along a telescope optical axis to focus collected light based on distance between the primary and secondary mirror, the collected light including an image of reflectance from the target surface of the interrogation beam at its transmission wavelength;
ii. an optical splitter along the optical axis after the primary and secondary mirrors to split received collected light into two paths:
(1) one path directed to the input ends of the fiber optic bundle for use at the imaging spectrometer;
(2) the other path directed to a photo-detector sensitive to the transmission wavelength of the interrogation beam collected from the target surface;
iii. an actuator in operative connection to at least one of the primary and secondary mirrors operatively connected to the photodetector to automatically adjust primary to secondary mirror distance based on measured intensity of the transmission wavelength of the interrogation beam to automatically focus the telescope.

10. The apparatus of claim 9 further comprising a position resolver in the telescope calibrated to estimate distance to the target surface based on sensed distance between the primary and secondary mirrors when automatically focused.

11. The apparatus of claim 9 further comprising limiting reflectance on the photodetector to approximately the diameter of the collected and focused interrogation beam.

12. A method of highly portable, standoff distance chemical sensing comprising:
a. configuring a compact imaging spectrometer by providing light comprising target surface reflectance through a linear array of a plurality of fiber optics, and collimating, diffracting, and imaging the light from the linear array of fiber optics in an image plane of a digital imager in a compact space, wherein each fiber optic of the linear array of fiber optics is correlated spatially to a portion of the target surface, further comprising
i. separately directing reflectance from the target surface, including an image of the incident light on the target surface, though primary and secondary lenses of a receiving telescope onto a photodetector and measuring intensity;
ii. adjusting the distance between the primary and secondary lenses to optimize intensity;
iii. assuming optimized intensity is optimized focusing of the receiving telescope;
b. conducting Raman spectroscopy on light from each said fiber optic of the linear array of fiber optics at the image plane;
c. comparing spectra from at least two said fiber optics of the linear array of fiber optics from different spatial correlations;
d. assuming that an offset between the compared spectra indicates a chemical species of interest at that spatial location and that the other spectra comprises noise or fluorescence; and
e. signaling presence of the chemical species of interest to a user interface.

13. The method of claim 12 wherein the number of fiber optics is hundreds and reflectance is received at a circular array at input ends of the fiber optics.

14. The method of claim 13 wherein the plural fiber optics are rearranged into a linear array at output ends.

15. The method of claim 12 wherein resolution between spectra at each fiber optic is on the order of 100 µm.

16. The method of claim 12 wherein the signaling comprises one or more of:
a. graphic or text content on a display;
b. haptic feedback;
c. audible feedback.

17. The method of claim 12 further comprising:
a. adding location and time data to information about the sensing event;
b. storing information about the sensing event;
c. simultaneous display of different information related to a sensing event.

18. The method of claim 12 further comprising:
a. sensing distance between the primary and secondary lenses upon sensing optimized intensity;
b. correlating the sensed distance to range to the target surface;
c. communicating the estimated range to the user interface.

19. The method of claim 12 wherein the user interface comprises a hand-held or wearable device in wireless communication with the imaging spectrometer.

20. The method of claim 12 used to detect presence of explosives.

* * * * *

UNITED STATES PATENT AND TRADEMARK OFFICE
CERTIFICATE OF CORRECTION

| | |
|---|---|
| PATENT NO. | : 10,663,404 B1 |
| APPLICATION NO. | : 16/151682 |
| DATED | : May 26, 2020 |
| INVENTOR(S) | : Robert Dean Babnick et al. |

Page 1 of 1

It is certified that error appears in the above-identified patent and that said Letters Patent is hereby corrected as shown below:

<u>In Column 15, Claim 9(c.)(iii.), Line 11:</u>
DELETE "toile" after "receiver"
INSERT --to the-- after "receiver"

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*